United States Patent
Salkovic et al.

(10) Patent No.: US 9,872,523 B2
(45) Date of Patent: Jan. 23, 2018

(54) PIECE OF CLOTHING FOR SUPPORTING SLEEP

(71) Applicants: Elvis Salkovic, Hamburg (DE); Sadat Salkovic, Hamburg (DE); Dariusch Feizollahi, Norderstedt (DE)

(72) Inventors: Elvis Salkovic, Hamburg (DE); Sadat Salkovic, Hamburg (DE); Dariusch Feizollahi, Norderstedt (DE)

( * ) Notice: Subject to any disclaimer, the term of this patent is extended or adjusted under 35 U.S.C. 154(b) by 0 days.

(21) Appl. No.: 15/154,391

(22) Filed: May 13, 2016

(65) Prior Publication Data
US 2017/0325515 A1 Nov. 16, 2017

(51) Int. Cl.
| A41D 11/00 | (2006.01) |
| A41B 13/06 | (2006.01) |
| A41B 13/00 | (2006.01) |
| A61B 5/01 | (2006.01) |
| A61B 5/00 | (2006.01) |
| A61B 5/103 | (2006.01) |

(52) U.S. Cl.
CPC ............ *A41B 13/065* (2013.01); *A41B 13/00* (2013.01); *A41B 13/005* (2013.01); *A61B 5/01* (2013.01); *A61B 5/1036* (2013.01); *A61B 5/6804* (2013.01)

(58) Field of Classification Search
CPC ........ A41B 13/00; A41B 13/06; A41D 10/00; A41D 13/0015
USPC ............................ 2/80, 83, 69; 128/873, 869
See application file for complete search history.

(56) References Cited

U.S. PATENT DOCUMENTS

| 2,908,912 A | * | 10/1959 | Darling | .................. | A47G 9/083 2/83 |
| 4,206,512 A | * | 6/1980 | Osborne | ................ | A41D 10/00 128/873 |
| 5,129,406 A | * | 7/1992 | Magnusen | ................ | A61F 5/37 128/845 |
| 2016/0113331 A1 | * | 4/2016 | Blacker | .................. | A41B 13/06 2/80 |

FOREIGN PATENT DOCUMENTS

| CA | 2831058 A1 * | 10/2012 | ........... A41B 13/005 |
| WO | WO 2012130771 A1 * | 10/2012 | ............... C07K 7/06 |

* cited by examiner

*Primary Examiner* — Tejash Patel
(74) *Attorney, Agent, or Firm* — Bay State IP, LLC

(57) ABSTRACT

The invention relates to a piece of clothing (1), in particular to a bodysuit or overall for infants and young children, made from an elastic material for variably wrapping up and for supporting the sleep of an infant or young child, which can be used to cover up at least the torso and at least partially the arms of the body of the infant or young child, comprising a torso section (2) and a sleeve section (3), wherein the torso section (2) is connected to the sleeve section (3) and the sleeve section (3) has at least two regions (4) for variably fixing the arms of the infant or young child, and fastening means (5) for variably wrapping up the infant or young child, wherein the fastening means (5) are at least partially attached in the two regions (4) of the sleeve section (3).

14 Claims, 2 Drawing Sheets

PIECE OF CLOTHING FOR SUPPORTING SLEEP

BACKGROUND OF THE INVENTION

Field of the Invention

The invention relates to a piece of clothing, in particular a bodysuit or an overall for infants and young children, made from an elastic material for variably wrapping up and supporting the sleep of an infant or young child, which can be used to cover up at least the torso and at least partially the arms of the body of the infant or young child, and a wristband for fixing to a sleeve section of a piece of clothing. Moreover, the invention relates to a method for producing a piece of clothing.

Description of the Related Art

Pucking refers to a special wrapping technique for tightly wrapping up new-born babies, in order to give them a feeling of security and tightness similar to the condition in the mother's womb during pregnancy. In the pucked condition, the arms of the new-born baby rest tightly against the body and any movement of the arms and the legs is very limited. This wrapping technique has been known for a very long time, since even in ancient times children were completely wrapped up, e.g. pucked.

Nowadays, the so-called pucking is very widespread amongst parents and midwives. Babies are mostly pucked just for several hours, for example for sleeping. As a result of the protective wrapping with clearly distinguishable and tangible limits, the baby feels protected and secure. Pucked babies often sleep longer and calmer, and the supine position recommended by paediatricians and by the World Health Organisation for sleeping is supported, as a result of which also the risk of sudden infant death syndrome can be reduced, and pucking can also be helpful for babies tending to cry. As a result of the tight wrapping and the feeling of security, new-born babies often sleep longer and calmer.

Usually, a so-called pucking cloth is used by parents and midwives, which is mostly a usual cloth or a usual cover of sufficient dimensions. The baby is for example centrally placed on the cloth, and the two sides are folded inwards over the baby and are fixed underneath the baby. The pucking cloth is made from a stretchable textile material. Further, so-called pucking bags are known which consist of a plurality of fabric layers or cloths sewn together, which are intended to simplify the pucking of the infant. A pucking bag should be appropriate for the size of the child and the ambient temperature, so that a plurality of pucking bags are necessary in order to account for different temperatures and the growth of the infant. An alternative to the use of cloths, covers or pucking bags is the use of strips.

Further, pucking suppresses the moro reflex of the child. In this reflex, jerky stretching of the arms, spreading out of the fingers and opening of the mouth occurs. In the course of this, the arms and legs of the infant fall apart in the supine position. As a result, many infants wake themselves up and begin to cry. However, this reflex may also be caused by fright situations and makes falling asleep difficult for some new-born babies, as a result of which overtiring and crying may occur.

Further disadvantages of pucking may be the development of more heat or the formation of a greater heat build-up, which may lead to the risk of heat stroke or dehydration. Further, pucking may cause trapped nerves, or there might simply not be enough room for the baby to breathe deeply or to cry. Further, the risk of hip misalignments, so-called hip dysplasia, is increased.

SUMMARY OF THE INVENTION

It is the object of the invention to provide a possibility for wrapping up or pucking infants or young children in a simple and reliable manner, whilst allowing a satisfactory pucking result to be achieved irrespective of the size and/or the width of the infant, i.e. it should be possible to puck infants of different sizes and/or widths in a simple, reliable and sufficiently firm manner whilst avoiding the need to carry along usual wrapping parts for the pucking.

This object is achieved by the independent claims. Advantageous embodiments are indicated in the dependent claims.

According to a first aspect of the invention this object is achieved by providing a piece of clothing, in particular a bodysuit or an overall for infants and young children, made from an elastic material for variably wrapping up and supporting the sleep of an infant or young child, which can be used to cover up at least the torso and at least partially the arms of the body of the infant or young child. The piece of clothing comprises a torso section and an arm section, wherein the torso section is connected to the arm section and the arm section has at least two regions for variably fixing the arms of the infant or young child, and fastening means for variably wrapping up the infant or young child, which fastening means are at least partially attached in the two regions of the arm section, so that the piece of clothing can be adapted in the region of the arms and/or of the torso to the body size and to the body shape of the infant or young child.

In this way, a possibility is provided to calm the child, to give them sufficient warmth and to allow them in this way to fall asleep easier and to sleep through better. Moreover, it is avoided that the child gets injured by their own arm movements, and at the same time the natural instinct for movement of the child and thus also the learning process of the brain that controls the motor function are promoted.

In particular, the piece of clothing may be an overall for a young child. An overall is a one-piece suit that substantially completely covers the torso, the arms and the legs of the wearer. Whilst a bodysuit usually lies directly on the skin of the wearer, an overall usually constitutes the top layer of clothing and is for example worn on top of a bodysuit or a vest or a pair of pants. In particular, an overall is of advantage for young infants because it allows the necessary freedom of movement for the young child and on the other hand ensures, as a result of being made in one piece, that the individual sections of the overall cannot slip. As a result it is avoided that individual body regions of the young child are uncovered and cool down. Further, an overall simplifies the wrapping up of the young child. Advantageously, such an overall not only protects the limbs of the wearer from hypothermia but also, as a result of the variable wrapping up, the heat can be regulated even during warm seasons, in particular this can be used to allow a natural freedom of movement for the arms and/or legs, and the arm position of the infant can be modified or adapted.

The expression "connected to each other" as used below means that the individual sections are permanently connected to each other, so that they cannot be separated from each other without destroying them. To this end, the respective sections of the piece of clothing may for example be sewn together. It is also possible for the respective sections of the piece of clothing to be formed in one piece, i.e. from a continuous fabric web or from a plurality of continuous fabric webs lying on top of each other. The variable wrapping up of the infant is carried out as needed, for example, supporting sleep can be ensured in a targeted manner by providing sufficient freedom for the arms.

The at least two regions are preferably attached to the respective sleeves of the piece of clothing, i.e. the arm section comprises both sleeves and each sleeve preferably has a region for variable fastening. To this end, the appropriate fastening means are selected and the non-selected fastening means remain unconnected. Advantageously, due to cuffs and/or strips on the leg sections, the piece of clothing can be adapted to the infant's body also in the region of the legs. The inventive concept can be applied in general to the region of a piece of clothing that covers the torso and at least partially the arms of the wearer thereof. Thus, it may be related not just to bodysuits or overalls, but also for example to jackets. Advantageously, the piece of clothing is made from a body-friendly, easy-to-clean fabric, for example from cotton or plush. However, also other types of fabrics, for example synthetic fabrics or combinations of natural and synthetic fibres may be used.

Advantageously, the piece of clothing may preferably be manufactured from cuddly soft cotton. It is a concept of the invention that the piece of clothing is ideal both for the summer and the winter season, since it allows a variable wrapping up of the infant or young child. Preferably, the piece of clothing has a pleasant soft, elastic and wide cuff and fits well around the body of the child. The generous form advantageously allows a lot of freedom of movement and sufficient room for the legs of the baby or the infant or young child. Contrary to firm wrapping, also kicking of the legs may be possible, whilst the young child is covered up at all times.

According to a preferred embodiment example of the invention, the fastening means and the fastening means made to be complementary thereto are attached in the torso section and/or distributed over the sleeve section in such a way that an effective width of the piece of clothing can be variably adjustable by fixing the one or more fastening means to the one or more fastening means formed to be complementary thereto.

The expression "distributed over the arm section" as used below also refers to the section outside of the two regions of the arm sections. The effective width of the piece of clothing is correlated with the strength of the wrapping or the pucking. Thus, the effective width of the piece of clothing can be variably adjusted. The piece of clothing can therefore be used for infants of different sizes and can grow together with the infant. Zips, Velcros, buttons, in particular pushbuttons, strips, hooks and/or eyelets are formed as fastening means. Moreover, the width and the circumference can be adjusted in the back and chest/tummy area in a variable and yet reliable and secure manner. Thus, a satisfactory pucking result may be achieved irrespective of the chest measurement of the infant.

According to another preferred embodiment example of the invention, the two areas of the arm section have a rail-like shape and the fastening means and/or the fastening means formed to be complementary thereto are slidable on the rail-like regions in a vertical direction in the torso section, so that the desired position of the arms of the infant or young child can be adjusted.

The expression "in the vertical direction" as used below refers to the direction in relation to the head and/or to the legs of the child. Thus, it is made possible to adjust the arms of the infant or young child as needed. The rail-like shape is advantageous in particular for zips and buttons as fastening means, because they can be simply and securely snapped into the rail or the rail profile.

According to a further preferred embodiment example of the invention, the two regions of the arm section have a strip-like shape, and the fastening means and/or the fastening means formed to be complementary thereto can be fixed to the strip-like regions in the vertical direction in the torso section, so that the desired position of the arms of the infant or young child can be adjusted. The desired position of the arms of the infant can also be adjusted by means of buttons and Velcros as the fastening means. Advantageously, also a combination of the rail and strip-like shape is possible. The elongated Velcro strips allow a simple yet efficient adjustment of the effective width of the piece of clothing or of the effective pucking width, so that the piece of clothing according to the invention can be used to puck infants of different widths or different chest sizes in a simple, reliable and sufficiently firm manner, in particular in the circumferential direction. This means that the upper body of the infant, including the arms, can be pucked in in a secure and tight manner irrespective of the width of the infant. Advantageously, the fastening means allow a simple and yet efficient adjusting of the effective width of the piece of clothing, so that the piece of clothing according to the invention can be used to puck infants of different sizes or lengths in a simple, reliable and sufficiently firm manner, in particular also in the longitudinal direction. This means that the legs and feet of the infant can be pucked in a firm manner also in the longitudinal direction. Advantageously, the Velcros allow the sleeves to be opened and re-closed with one hand, without the front and rear sides of the sleeves having to be accurately positioned relative to each other.

Since in particular young children in the first months of their lives grow very quickly, it is of advantage to provide a plurality of rows of fastening means in the torso section and/or in the arm section, in order to be able to follow the growth of the young child in this region at least within certain limits and to be able to correspondingly adapt the piece of clothing. As a result, the fitting of the piece of clothing is improved and any pressure or abrasion points are prevented. Moreover, as a result of the variable wrapping up of the young child, nappies of different thicknesses can be taken into account, for example a thinner nappy during the day and a thicker nappy during the night.

According to a preferred embodiment example of the invention, a temperature sensor is provided that is at least partially integrated into the elastic material and is suitable for measuring the temperature within the piece of clothing. Thus, a possibility of measuring the temperature within the piece of clothing or in the vicinity of the baby's body at any time is provided, so that the different heat requirements of the child during different seasons and/or during different times of the day can be taken into account. Moreover, it is possible to adjust a feel-good temperature for the infant in a targeted manner that does not cause the infant to sweat.

According to another preferred embodiment example of the invention, a pressure sensor is provided in the arm section and/or in the torso section, which is at least partially integrated into the elastic material and is suitable for measuring the force acting on the infant or the young child. In this way, a possibility is provided to measure the force acting on the young child, so that it can be checked whether the strength of the wrapping or of the pucking is appropriate or whether it needs to be changed.

According to a preferred embodiment example of the invention, a display is provided on the surface of the elastic material, and this display is coupled to the temperature sensor and is suitable for displaying the temperature measured by the temperature sensor. As a result it is made possible, without opening the piece of clothing, to read the temperature directly from the display on a surface of the piece of clothing.

According to another preferred embodiment example of the invention, a display is provided on a surface of the elastic material, which display is coupled to the pressure sensor and is suitable for indicating the force measured by the pressure sensor in the arm section and/or in the torso section. In this way, the strength of the pucking can be monitored and adapted. Also a combination of the temperature sensor and of the pressure sensor is possible, and the measured values can be indicated on the same display or on different displays.

Advantageously, the fastening means can be used to adapt the piece of clothing to the different sizes of the child in the torso region as well as in the region of the arms and of the legs, so that the piece of clothing can be adapted to any body size of the child and can grow together with the new-born baby. Further, the at least partially integrated temperature sensor and/or pressure sensor can help to minimise the risk of overheating and/or overloading the child. This may be particularly advantageous if the baby suffers from a feverish infection. Moreover, a degree of movement may be provided or adjusted, so that in particular in the case of prematurely born babies the loose pucking can be used to hold the weak and not very movable arms on the body of the child. In this way, also movements that can already be carried out by the prematurely born baby may be facilitated. The extremely retarded motoric development of such children requires the simulation of the previously "weightless" condition of the arms in the aqueous medium of the uterus. Therefore, the arms of these prematurely born babies are wrapped in flexion rather than in extension. Moreover, the hands are placed close to the mouth. This position allows self-calming, which in the case of the usual wrapping up is exactly what is prevented.

According to a second aspect of the invention, the object is achieved by providing a wristband for fixing to a sleeve section of the piece of clothing according to the first aspect of the invention, which wristband includes an elastic material and fastening means, which fastening means are attached to a surface of the elastic material, so that the arms of the body of the infant or young child can be completely covered up. Thus, the sleeve section of the piece of clothing can be variably extended, which is desired especially during the colder season.

Advantageously, the wristband can be bought separately and its width can be varied owing to the elastic material and/or the fastening means. In addition, a pulse monitor may be integrated in the wristband, and this pulse monitor is coupled with a display, so that the measured pulse is indicated on the display on the wrist of the infant.

According to a third aspect of the invention, the object is achieved by providing a method for producing a piece of clothing, in particular of a bodysuit or an overall for infants and young children, according to the first aspect of the invention, which method comprises the following steps: a) attaching at least two regions for variably fastening the arms of the infant or young child in a sleeve section of the piece of clothing, and connecting a torso section to the sleeve section, wherein the torso section and the sleeve section include an elastic material, and b) attaching fastening means at least partially in the two regions of the sleeve section.

BRIEF DESCRIPTION OF THE DRAWINGS

The invention will be explained in more detail below by means of preferred embodiment examples with reference to the drawings.

DETAILED DESCRIPTION OF THE SEVERAL EMBODIMENTS

Figure 1:
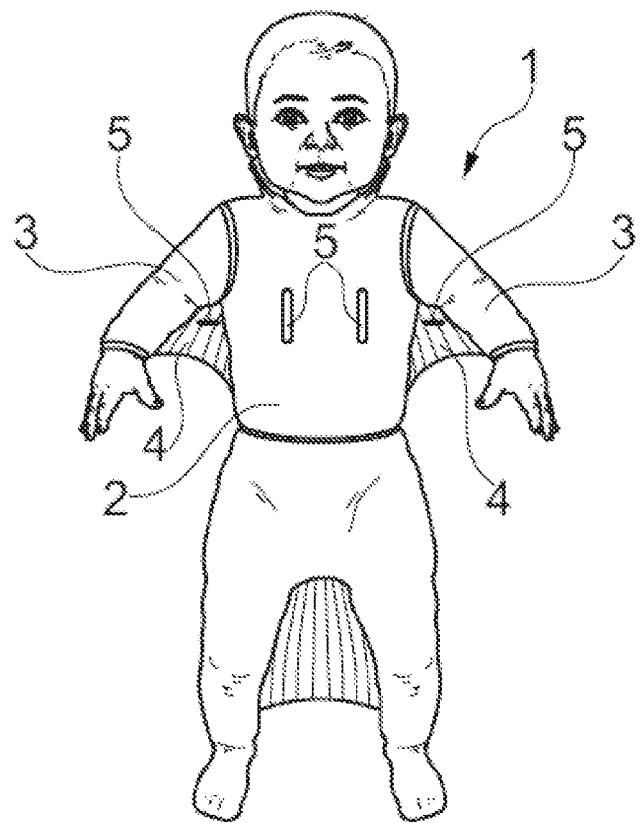
FIG. 1 shows a young child in a piece of clothing according to a first preferred embodiment example of the invention.

FIG. 1 shows a young child in a piece of clothing 1 according to a first preferred embodiment example of the invention. The piece of clothing 1 comprises a torso section 2 and a sleeve section 3, which are permanently connected to each other. In this first preferred embodiment example of the invention, two regions 4 for variably fastening the arms of the young child to the sleeve section 3 are provided. Further, fastening means 5 for variably wrapping up the young child are provided, which fastening means 5 are attached in the two regions 4 of the sleeve section 3, and the fastening means 5 formed to be complementary thereto are attached in the torso section 2. As the fastening means, Velcro strips 5 are provided in this first preferred embodiment example. The piece of clothing 1 covers the torso, the arms and the legs of the young child, i.e. only the hands and the head of the young child remain uncovered in this first embodiment example.

Figure 2:
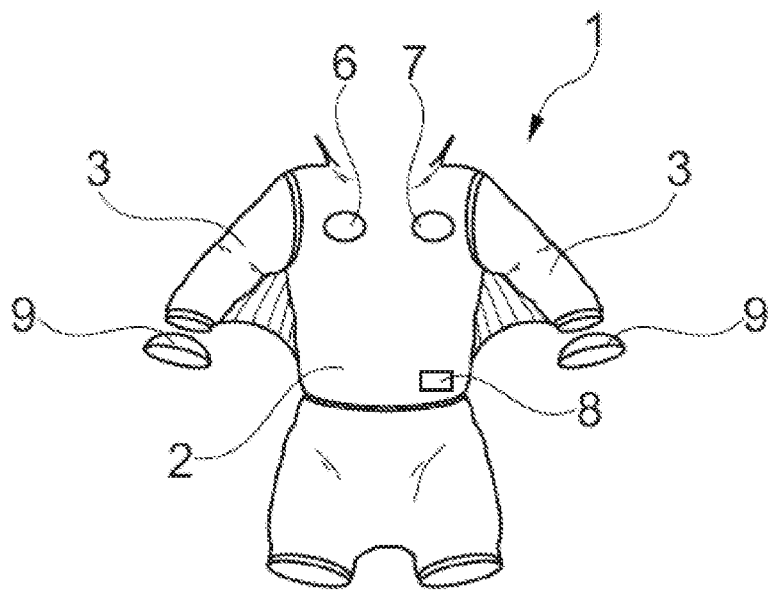
FIG. 2 shows a piece of clothing and wristbands according to a second preferred embodiment example of the invention.

FIG. 2 shows a piece of clothing 1 and two wristbands 9 according to a second preferred embodiment example of the invention. In this second preferred embodiment example, the piece of clothing 1 has a short leg section. The sleeve section 3 is also short, but can be appropriately extended by fastening or attaching one or both of the wristbands 9. Further, a temperature sensor 6 and a pressure sensor 7 are integrated into the elastic material of the piece of clothing 1 and are coupled with a display 8, which display 8 indicates the measured temperature and force in the torso section 2. Thus, parents or midwives can control the temperature in the piece of clothing and the force acting on the baby at any time. This provides the possibility of improving the effective width of the piece of clothing and thus of the temperature and/or of the force.

Figure 3:
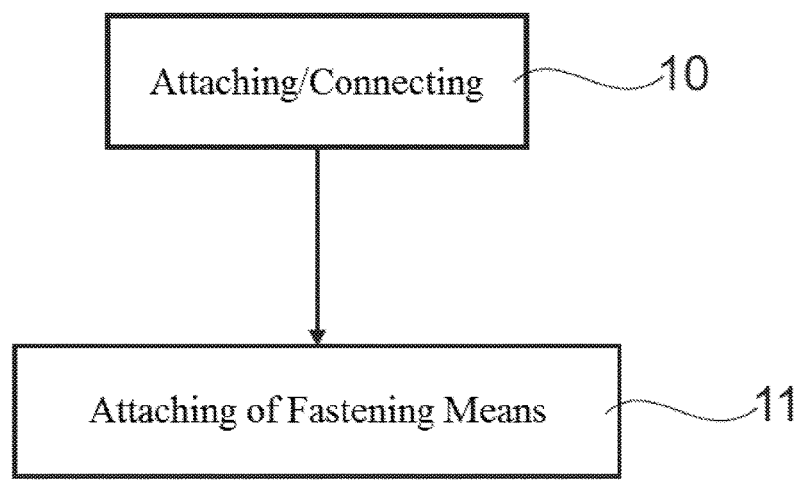
FIG. 3 shows the steps of a method for producing a piece of clothing according to a third preferred embodiment example of the invention.

FIG. 3 shows the steps of a method according to a third preferred embodiment example of the invention. In a first step of the method, at least the two regions 4 for variably fixing the arms of the infant in a sleeve section 3 of the piece of clothing 1 are attached 10, and a torso section 2 of the piece of clothing 1 is connected to the sleeve section 3, and both the torso section 2 and the sleeve section 3 include an elastic material. In a second step, the fastening means 5 are attached 11 at least partially in the two regions 4 of the sleeve section 3. Further, the fastening means 5 may also be attached in the torso section 2, so that the piece of clothing 1 can be adapted to the body size and the body shape of the young child both in the region of the arms and of the torso. In further steps, temperature and/or pressure sensors or displays may be attached.

What is claimed is:

1. A piece of clothing, in particular a bodysuit or overall for infants and young children, made from an elastic material for variably wrapping up and supporting the sleep of an infant or young child, which can be used to cover up at least the torso and at least partially the arms of the body of the infant or young child, comprising:

a torso section (2) and two sleeve sections (3), wherein the torso section (2) is connected to the sleeve sections (3) and the sleeve sections (3) have at least two regions (4) for variably fixing the arms of the infant or young child, and fastening means (5) for variably wrapping up the infant or young child, wherein the fastening means (5) are at least partially attached in the two regions (4) of the sleeve section (3), so that the piece of clothing (1) can be adapted to the body size and the body shape of the infant or young child in the region of the arms and/or of the torso.

2. The piece of clothing as claimed in claim 1, wherein the fastening means (5) and the fastening means (5) formed to be complementary thereto are attached in a distributed manner in the torso section (2) and/or over the sleeve section (3), so that an effective width of the piece of clothing can be variably adjusted by fastening the one or more fastening means (5) to the one or more fastening means (5) formed to be complementary thereto.

3. The piece of clothing as claimed in claim 1, wherein the at least two regions (4) of the sleeve section (3) have a rail-like shape and the fastening means (5) and/or the fastening means (5) formed to be complementary thereto are slidable on the rail-like regions in a vertical direction in the torso section (2), so that the desired position of the arms of the infant or young child can be adjusted.

4. The piece of clothing as claimed in claim 1, wherein the at least two regions (4) of the sleeve section (3) have a strip-like shape and the fastening means (5) or the fastening means (5) that are formed to be complementary thereto can be fixed to the strip-like regions in the vertical direction in the torso section (2), so that the desired position of the arms of the infant or young child can be adjusted.

5. The piece of clothing as claimed in claim 1, wherein a temperature sensor (6) is provided that is integrated at least partially in the elastic material and is suitable for measuring the temperature within the piece of clothing (1).

6. The piece of clothing as claimed in claim 1, wherein a pressure sensor (7) is provided in the sleeve section (3) or in the torso section (2), which is at least partially integrated into the elastic material and is suitable for measuring the force acting on the infant or the young child.

7. The piece of clothing as claimed in claim 5, wherein a display (8) is provided on the surface of the elastic material, which display (8) is coupled with the temperature sensor (6) and is suitable for indicating the temperature measured by the temperature sensor (6).

8. The piece of clothing as claimed in claim 6, wherein a display (8) is provided on a surface of the elastic material, which display (8) is coupled with the pressure sensor (7) and is suitable for indicating the force measured by the pressure sensor (7) in the sleeve section (3) or in the torso section (2).

9. A wristband (9) for fastening to a sleeve section (3) of the piece of clothing (1) as claimed in claim 1, wherein the wristband (9) includes an elastic material and fastening means, wherein the fastening means (5) are attached to a surface of the elastic material, so that the arms of the body of the infant or young child can be completely covered up.

10. A method for producing a piece of clothing (1), in particular a bodysuit or an overall for infants and young children as claimed in claim 1, comprising the following steps:

attaching (10) the at least two regions (4) for variably fixing the arms of the infant or the young child in a sleeve section (3) of the piece of clothing (1) and connecting a torso section (2) to the sleeve section (3), wherein the torso section (2) and the sleeve section (3) include an elastic material; and attaching (11) fastening means (5) at least partially in the two regions (4) of the sleeve section (3).

11. The piece of clothing as claimed in claim 1, wherein the fastening means (5) formed to be complementary thereto are attached in a distributed manner in the torso section (2) and over the sleeve section (3), so that an effective width of the piece of clothing can be variably adjusted by fastening the one or more fastening means (5) to the one or more fastening means (5) formed to be complementary thereto.

12. The piece of clothing as claimed in claim 1, wherein the two regions (4) of the sleeve section (3) have a strip-like shape and the fastening means (5) that are formed to be complementary thereto can be fixed to the strip-like regions in the vertical direction in the torso section (2), so that the desired position of the arms of the infant or young child can be adjusted.

13. The piece of clothing as claimed in claim 1, wherein a pressure sensor (7) is provided in the sleeve section (3) and in the torso section (2), which is at least partially integrated into the elastic material and is suitable for measuring the force acting on the infant or the young child.

14. The piece of clothing as claimed in claim 7, wherein a display (8) is provided on a surface of the elastic material, which display (8) is coupled with the pressure sensor (7) and is suitable for indicating the force measured by the pressure sensor (7) in the sleeve section (3) and in the torso section (2).

\* \* \* \* \*